United States Patent [19]

Horner et al.

[11] 4,353,836
[45] Oct. 12, 1982

[54] 4-(2,5-DIHYDROXYPHEN-1-YL)-CROTONIC ACID AND ITS DERIVATIVES, AND THE PREPARATION OF THESE COMPOUNDS

[75] Inventors: Michael Horner, Neustadt; Axel Nissen, Leimen, both of Fed. Rep. of Germany

[73] Assignee: BASF Aktiengesellschaft, Fed. Rep. of Germany

[21] Appl. No.: 238,609

[22] Filed: Feb. 26, 1981

[30] Foreign Application Priority Data

Mar. 19, 1980 [DE] Fed. Rep. of Germany ....... 3010474

[51] Int. Cl.³ .................. C07C 69/28; C07C 69/734; C07C 59/64
[52] U.S. Cl. .................................. 260/410.5; 560/55; 560/75; 560/144; 562/465; 562/478
[58] Field of Search .......................... 560/75, 55, 144; 562/478, 465, 435; 260/396 R, 410.5

[56] References Cited

U.S. PATENT DOCUMENTS

| | | | |
|---|---|---|---|
| 3,825,584 | 7/1974 | Morimoto et al. | 560/75 |
| 3,947,473 | 3/1976 | Scott et al. | 560/75 |
| 4,139,545 | 2/1979 | Morimoto et al. | 560/55 |

*Primary Examiner*—Natalie Trousof
*Assistant Examiner*—L. Hendriksen
*Attorney, Agent, or Firm*—Keil & Witherspoon

[57] ABSTRACT

4-(2,5-Dihydroxyphen-1-yl)-crotonic acid and its derivative (I)

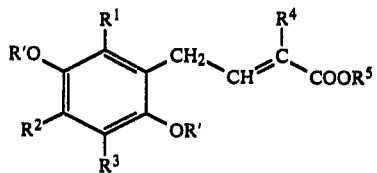

where $R^1$, $R^2$, $R^3$ and $R^4$ are each H or $C_1$-$C_8$-alkyl, $R^5$ is H, $C_1$-$C_{30}$-alkyl or $C_2$-$C_{30}$-alkenyl, and R' is H or an organic radical which can be split off hydrogenolytically, and a process for the preparation of the compounds I, wherein a hydroquinone II

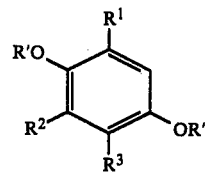

is reacted, in the presence of from 0.1 to 2 moles of a Lewis acid per mole of II, with
(a) a vinylglycolic acid derivative IIIa

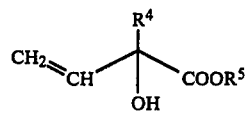

or
(b) a crotonic acid derivative IIIb

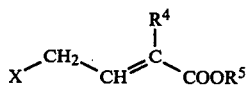

where X is halogen, hydroxyl or $C_1$-$C_4$-alkoxy or acyloxy.

3 Claims, No Drawings

4-(2,5-DIHYDROXYPHEN-1-YL)-CROTONIC ACID AND ITS DERIVATIVES, AND THE PREPARATION OF THESE COMPOUNDS

The present invention relates to 4-(2,5-dihydroxyphen-1-yl)-crotonic acid and its derivatives, of the general formula I

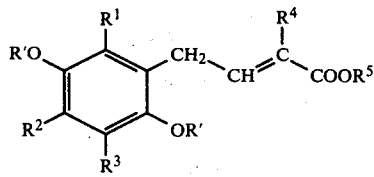

where $R^1$, $R^2$, $R^3$ and $R^4$ are each H or $C_1$-$C_8$-alkyl, $R^5$ is H, $C_1$-$C_{30}$-alkyl or $C_2$-$C_{30}$-alkenyl, and $R'$ is H or an organic radical which can be split off hydrolytically or hydrogenolytically.

The invention also relates to the preparation of these compounds.

It is well known that compounds which contain a hydroquinone structure in the molecule may be used as light stabilizers, heat stabilizers and oxidation stabilizers for organic materials, especially plastics. Examples of such compounds are α-tocopherol

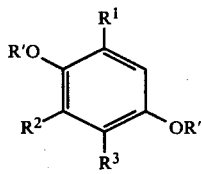

and chroman derivatives structurally related thereto.

It is an object of the present invention to provide novel hydroquinone derivatives which can themselves be used as stabilizers or which may be used to prepare stabilizers of the above type, and which generally extend synthesis capabilities in this field.

We have found that this object is achieved by providing the novel compounds defined at the outset, which are obtained when a hydroquinone II

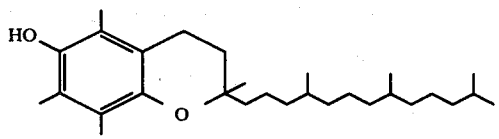

is reacted, in the presence of from 0.1 to 2 moles of a Lewis acid per mole of II, with (a) a vinylglycolic acid derivative IIIa

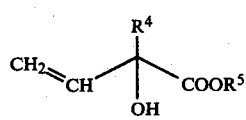

or (b) a crotonic acid derivative IIIb

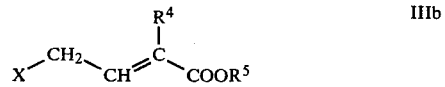

where X is halogen, hydroxyl or $C_1$-$C_4$-alkoxy or acyloxy.

Examples of suitable Lewis acids are $BF_3$, $AlCl_3$, $ZnBr_2$, $ZnI_2$ and especially $ZnCl_2$, these being used preferably in amounts of from 0.2 to 1 mole per mole of II. The simultaneous use of from 1 to 5 moles of a strong anhydrous inorganic acid per mole of Lewis acid is particularly advantageous; such inorganic acids are in particular HCl and HBr.

Preferably, the compounds II and IIIa or IIIb are reacted in an equimolar ratio, but it can be advantageous to employ IIIa or IIIb in up to 1.5-molar excess.

Preferably, both embodiments (a) and (b) of the process are carried out in the presence of an inert aprotic solvent having a donicity of at most 20. The donicity, defined in Angew. Chemie, 82 (1972), 858 is a measure of the stability of complex compounds of Lewis acids and solvents. Accordingly, suitable solvents are those which are weakly complex-forming, eg. benzene, chlorobenzene, nitromethane, acetonitrile, methylene chloride, 1,2-dichloroethane, chloroform and especially n-hexane, n-heptane and toluene. The function of the solvent is to keep part or all of the reactants in solution.

This determines the amount of solvent, which can vary within wide limits but is in general from 5 to 15 kg per kilogram of II.

The reaction temperature is preferably from 30 to 150° C., especially from 60° to 130° C. Since the reaction can be carried out under atmospheric pressure, working under reduced or superatmospheric pressure is in general not necessary.

The reaction is carried out in accordance with the conventional preparative techniques of the Friedel-Crafts reaction, by, for example, mixing compound II and the Lewis acid and gradually adding IIIa or IIIb, at the reaction temperature. If a strong inorganic acid is also used, about half of this acid is added to the initial mixture and the other half is introduced in the course of the reaction. In all cases it is advantageous to stir the reaction mixture thoroughly and exclude air during the reaction, because of the sensitivity of the reactants to oxidation.

After completion of the reaction, which normally requires from 3 to 10 hours, the reaction mixture is worked up in a conventional manner by adding water and isolating product I from the organic phase. The yields of I are in general from 50 to 75%.

Amongst the products I, those where $R^1$, $R^2$, $R^3$ and $R^4$ are methyl are the most important.

If the compounds I are to be used as stabilizers per se, $R^5$ is preferably $C_{10}$-$C_{30}$-alkyl or alkenyl.

Compounds I used as intermediates are in particular those where $R^5$ is hydrogen. If $R'$ is not hydrogen but one of the protective groups included in the definition, then it is especially methyl, tert.butyl or benzyl, since these groups can be particularly easily removed again, by hydrolysis or hydrogenolysis. In general, preferred meanings of $R'$, other than hydrogen, are $C_1$-$C_8$-alkyl or acyl, or benzyl which is unsubstituted or carries inert substituents.

The starting compounds II, IIIa and IIIb from which the compounds I are derived are known or may be obtained by conventional methods.

The compounds I may be converted to chroman derivatives by methods illustrated in the following Example:

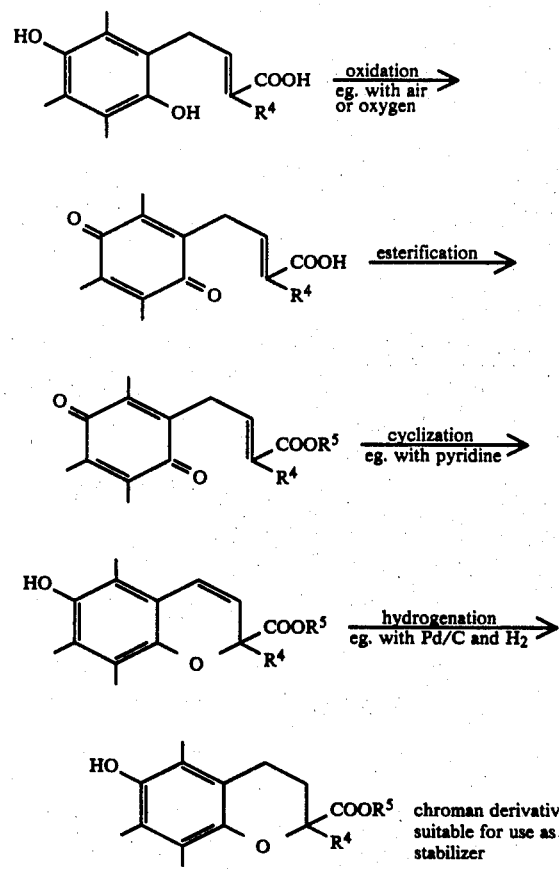

EXAMPLE 1

4-(2,5-Dihydroxy-3,4,6-trimethylphen-1-yl)-2-methylcrotonic acid, prepared by method (a)

A mixture of 24 g (0.2 mole) of vinyl-lactic acid and 10 g (0.07 mole) of anhydrous $ZnCl_2$ was boiled, with thorough stirring and with exclusion of air. 1 liter of anhydrous hydrogen chloride gas was then passed in over 15 minutes, and 30.4 g (0.2 mole) of trimethylhydroquinone were added over a further 45 minutes. A further 200 ml of HCl gas were then passed in, after which the mixture was refluxed for 4 hours to complete the reaction. Conventional working up gave the above product in 65% yield; melting point 208° C. (with decomposition).

EXAMPLE 2

4-(2,5-Dihydroxy-3,4,6-trimethylphen-1-yl)-2-methylcrotonic acid, prepared by method (b)

3 liters of HCl gas were passed, over one hour, into a mixture, heated to 98° C., of 9.0 g (0.06 mole) of trimethylhydroquinone, 8.0 g (0.06 mole) of 4-chloro-2-methylcrotonic acid, 3 g (0.02 mole) of anhydrous $ZnCl_2$ and 80 ml of heptane. After the mixture had been stirred for two hours, the heptane phase was decanted and the oily residue which remained was stirred for 24 h with methanol at 20° C. Hereupon, a part of the product crystallized out. The remainder was precipitated from the methanol phase by means of water. The crystals and the precipitate were combined and recrystallized from water. The yield of the above product was 62%.

EXAMPLE 3

Methyl 4-(2,5-dihydroxy-3,4,6-trimethylphen-1-yl)-2-methylcrotonate 23 g (0.34 mole) of $BF_3$ were passed, over 45 minutes, into a stirred solution of 34 ml of nitromethane and 250 ml of toluene at 0° C. 51.4 g (0.34 mole) of 2,3,5-trimethylhydroquinone were then added to the solution, followed by 44.2 g (0.34 mole) of methyl vinyl-lactate introduced in the course of 3 hours. After the reaction mixture had been additionally stirred for 10 hours at 15° C., it was worked up in a conventional manner; the above product was obtained in 20% yield; melting point 109°–111° C.

EXAMPLE 4 n-Heptyl 4-(2,5-dihydroxy-3,4,6-trimethylphen-1-yl)-2-methylcrotonate

The above compound was prepared in 15% yield by a method similar to Example 3, but starting from n-heptyl vinyl-lactate; melting point 39°–42° C.

We claim:

1. 4-(2,5-Dihydroxyphen-1-yl)-crotonic acid and its derivatives of the general formula I

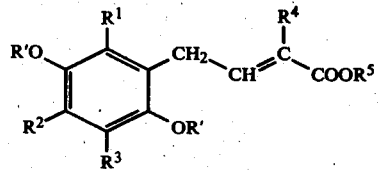

where $R^1$, $R^2$, $R^3$ and $R^4$ are each H or $C_1$–$C_8$-alkyl, $R^5$ is H, $C_1$–$C_{30}$-alkyl or $C_2$–$C_{30}$-alkenyl, and R' is H or an organic radical which can be split off hydrolytically or hydrogenolytically.

2. A compound of the formula I as set forth in claim 1, wherein R' is hydrogen.

3. A compound of the formula I of claim 1, wherein R' is $C_1$–$C_8$-alkyl or acyl, or benzyl which is unsubstituted or carries inert substituents.

* * * * *